US009302523B2

(12) United States Patent
Lopez Quintela et al.

(10) Patent No.: US 9,302,523 B2
(45) Date of Patent: Apr. 5, 2016

(54) USE OF LUMINESCENT NANOCOMPOUNDS FOR AUTHENTICATING SECURITY DOCUMENTS

(71) Applicants: Fabrica Nacional De Moneda y Timbre-Real Casa de la Moneda, Madrid (ES); Nanogap Sub-NM Powder, Sociedad Anonima, Ames (ES)

(72) Inventors: Manuel Arturo Lopez Quintela, Santiago de Compostela—A Coruna (ES); Vicente Garcia Juez, Madrid (ES)

(73) Assignees: FABRICA NACIONAL DE MONEDA Y TIMBRE—REAL CASA DE LA MONEDA, Madrid (ES); NANOGAP SUB-NM POWDER, SOCIEDAD ANONIMA, Ames, A Coruña (ES)

( * ) Notice: Subject to any disclaimer, the term of this patent is extended or adjusted under 35 U.S.C. 154(b) by 0 days.

(21) Appl. No.: 14/650,309

(22) PCT Filed: Dec. 11, 2013

(86) PCT No.: PCT/EP2013/076207
§ 371 (c)(1),
(2) Date: Jun. 7, 2015

(87) PCT Pub. No.: WO2014/090867
PCT Pub. Date: Jun. 19, 2014

(65) Prior Publication Data
US 2015/0306893 A1 Oct. 29, 2015

(30) Foreign Application Priority Data

Dec. 12, 2012 (EP) ..................................... 12382496

(51) Int. Cl.
*G01N 21/64* (2006.01)
*B41M 3/14* (2006.01)
(Continued)

(52) U.S. Cl.
CPC ................ *B41M 3/144* (2013.01); *C09K 11/58* (2013.01); *C22C 5/02* (2013.01); *C22C 5/06* (2013.01); *G01N 21/64* (2013.01); *G01N 21/6408* (2013.01)

(58) Field of Classification Search
CPC .. C09K 11/06; C09K 11/025; G01N 21/6428; G01N 33/582; G01N 21/64
See application file for complete search history.

(56) References Cited

U.S. PATENT DOCUMENTS

2002/0021003 A1* 2/2002 McGrew ......................... 283/93
2005/0001038 A1    1/2005 Walter et al.
(Continued)

FOREIGN PATENT DOCUMENTS

WO    2012090034 A1    7/2012
WO    2012172018 A1    12/2012

OTHER PUBLICATIONS

Das, R., et al., "Preparation of linoleic acid capped gold nanoparticles and their spectra", "Physica E", Jul. 18, 2010, pp. 224-227, vol. 43.
(Continued)

*Primary Examiner* — Marcus Taningco
(74) *Attorney, Agent, or Firm* — Hultquist, PLLC; Steven J. Hullquist (57) ABSTRACT

The present invention relates to the use of nanocompounds as non deactivable security markers comprising a charge-transfer complex of at least two different size metal atomic quantum clusters (AQCs). These nanocompounds are luminescent, particularly fluorescent after external excitation. The invention also relates to security documents, articles or elements incorporating these markers as well as to a method and a system for detecting the same.

18 Claims, 4 Drawing Sheets

(51) Int. Cl.
*C22C 5/02* (2006.01)
*C22C 5/06* (2006.01)
*C09K 11/58* (2006.01)

(56) References Cited

U.S. PATENT DOCUMENTS

| | | |
|---|---|---|
| 2007/0138295 A1 | 6/2007 | White |
| 2007/0275244 A1 | 11/2007 | Handrosch et al. |
| 2008/0265176 A1* | 10/2008 | Chauhan et al. ........... 250/459.1 |
| 2009/0035852 A1 | 2/2009 | Lopez Quintela et al. |
| 2009/0206162 A1 | 8/2009 | De Cremer et al. |
| 2009/0256116 A1 | 10/2009 | Shumaker-Perry et al. |
| 2010/0140501 A1 | 6/2010 | Lawandy |
| 2010/0270504 A1 | 10/2010 | Qu |
| 2011/0165689 A1 | 7/2011 | Ying et al. |
| 2011/0305919 A1* | 12/2011 | Conroy et al. ................ 428/615 |
| 2012/0187341 A1 | 7/2012 | Strek et al. |
| 2014/0103226 A1 | 4/2014 | Lopez Quintela et al. |

OTHER PUBLICATIONS

Douliez, J., et al., "Synthesising gold nanoparticles within bola fatty acid nanosomes", "Journal of Colloid and Interface Science", May 27, 2009, pp. 610-613, vol. 337.

Zheng, J., et al., "Individual Water-Soluble Dendrimer-Encapsulated Silver Nanodot Flourescence", "J. Am. Chem. Soc.", Oct. 31, 2002, pp. 13982-13983, vol. 124.

Zheng, J., et al., "Highly Fluorescent, Water-Soluble, Size-Tunable Gold Quantum Dots", "Phys. Rev. Lett.", Aug. 13, 2004, pp. 077402-1-077402-4, vol. 93, No. 7.

* cited by examiner

USE OF LUMINESCENT NANOCOMPOUNDS FOR AUTHENTICATING SECURITY DOCUMENTS

CROSS-REFERENCE TO RELATED APPLICATIONS

This application is a U.S. national phase under the provisions of 35 U.S.C. §371 of International Patent Application No. PCT/EP13/76207 filed Dec. 11, 2013, which in turn claims priority of European Patent Application No. EP12382496.3 filed Dec. 12, 2012. The disclosures of such international patent application and European priority patent application are hereby incorporated herein by reference in their respective entireties, for all purposes.

FIELD OF THE INVENTION

The present invention relates to charge-transfer (CT) complexes of metal atomic quantum clusters (AQCs), optionally coordinated with organic ligands, for the use thereof as carriers of authentication or anti-forgery features in security documents or articles.

BACKGROUND

As demonstrated by the huge number of patents existing in this field, the use of different security elements making the forgery of documents difficult has been extended in recent years. Some of these elements are detectable by human beings; meanwhile other security elements which are incorporated into documents require the use of special tools for detection thereof. These tools include spectroscopic methods such as UV-VIS absorption spectroscopy, fluorescence emission spectroscopy, IR spectroscopy or Raman spectroscopy.

Thus, luminescence pigments or substances have been incorporated into various security documents for certifying the authenticity thereof, the detection or observation of which requires the use of an excitation light in a particular region of wavelengths (for example UV light).

Today, the only fluorescent systems known having huge Stokes' displacement of greater than 200 nm and slow decaying times of more than microsecond are based on rare earth ions. However, they present multiple drawbacks such as: the difficulty in incorporating thereof in matrices such that they do not lose their fluorescent characteristics; the existence of fixed and particular excitation, emission and Stokes' displacement characteristics corresponding to each rare earth, therefore they are not susceptible to being changed, and they are expensive and scarce materials. Examples of these rare earth luminescent systems as security markers are described in documents U.S. Pat. No. 4,598,205, U.S. Pat. No. 4,452,843 and U.S. Pat. No. 4,463,970.

Therefore, there is a clear need to develop new compositions and methods which make forging security documents difficult.

BRIEF DESCRIPTION OF THE INVENTION

Surprisingly, the authors of the present invention have discovered fluorescent nanocompounds in the form of charge-transfer complexes of AQCs with huge Stokes' shifts and decaying times much greater than those described in the state of the art which do not use rare earth elements. The nanometric size of these complexes favors its use for authenticating security documents. Furthermore, its method of synthesis, allows the inventors to select the size of the AQCs, i.e. to select the excitation and emission wavelengths, and therefore to select the desired Stokes shift for the marker for a security document, article or element.

These nanocompounds comprise a charge-transfer complex of at least two different size metal atomic quantum clusters (AQCs), $M_n$ and $M'_{n'}$, of formula (I):

$$M_n^+ M'_{n'}{}^- \qquad (I),$$

wherein the metals, M and M', of the metal AQCs are the same or different metals, $M_n$, is the smaller AQC which is present in its oxidized form, $M_n^+$, $M'_{n'}$, is the larger AQC which is present in its reduced form, $M'_{n'}{}^-$, $M_n^+$ and $M'_{n'}{}^-$ are bound by electrostatic interactions, n and n' are respectively the number of metal atoms of M and M', and n is smaller than n'.

The excitation and emission wavelengths depend on the size of the AQCs present in the charge-transfer complex. The excitation and emission wavelengths can be selected at will directing the formation of AQCs of necessary sizes. Thus, the Stokes shift to be obtained can be selected at will, thus releasing the fixed and particular imposition that exists in rare earth-based fluorescence methods. Furthermore, due to the characteristics of the AQCs used there is no photobleaching.

Metal transition elements such as Au or Ag, for example, which are not toxic when present in very low concentrations, can be used. Furthermore, the great natural abundance of these elements makes this a completely sustainable method. The luminescent nanocompounds, i.e. the charge-transfer complexes bound or not to organic ligands, synthesized:

- are stable without loss of their properties over a period of at least one year stored under natural light and room temperature,
- are stable in the pH range of 3 to 10,
- can be concentrated until dry without losing their fluorescents properties even in dried form,
- can be redissolved once dried without losing their fluorescents properties, and also
- are used at a concentration less than that used in rare earth element-based luminescent systems.

The charge-transfer complex may be additionally bound to organic ligands, which can be further functionalized in its outer surface for the use thereof in different environments, e.g. in order to be introduced into a security element, article or document. In a particular embodiment the organic ligands are ω-hydroxyacids and ω-mercaptoacids ligands.

Therefore, one aspect of the invention refers to the use of the nanocompounds defined above, i.e. to the use of a charge-transfer complex of at least two different size metal atomic quantum clusters (AQCs), $M_n$ and $M'_{n'}$, of general formula (I):

$$M_n^+ M'_{n'}{}^- \qquad (I),$$

wherein the metals, M and M', of the metal AQCs are the same or different metals, $M_n$, is the smaller AQC which is present in its oxidized form, $M_n^+$, $M'_{n'}$, is the larger AQC which is present in its reduced form, $M'_{n'}{}^-$, $M_n^+$ and $M'_{n'}{}^-$ are bound by electrostatic interactions, n and n' are respectively the number of metal atoms of M and M', and n is smaller than n' as a marker for a security document, article or element.

In one embodiment the metals, M and M', of the metallic AQCs are selected from transition metals or combinations thereof, preferably the transition metals are selected from the group consisting of Au, Ag, Co, Cu, Pt, Fe, Cr, Pd, Ni, Rh and combinations thereof, more preferably they are selected from the group consisting of Au, Ag, Cu and combinations thereof, and more preferably the transition metals are selected from the group consisting of Au, Ag and the combination thereof.

In another embodiment the number of metal atoms, n and n', of the at least two different size metal atomic quantum clusters are:
- between 2 and 309 metal atoms,
- between 2 and 102 metal atoms,
- between 2 and 55 metal atoms, and
- between 2 and 25 metal atoms.

In a further embodiment the difference between n and n' is between 5 and 50 atoms or between 5 and 25 atoms.

In a preferred embodiment the charge-transfer complex is additionally bound to organic ligands, preferably selected from ω-hydroxyacids and ω-mercaptoacids ligands, which are attached to the atomic quantum clusters, $M_n$ and $M'_{n'}$.

In another embodiment after exciting the charge-transfer complex by an external excitation source luminescence, preferably fluorescence, is produced in the charge-transfer complex.

In a further embodiment the Stokes shift of the charge-transfer complex produced after exciting the charge-transfer complex by an external excitation source, is greater than approximately 150 nm, preferably greater than approximately 300 nm.

In another further embodiment, after exciting the charge-transfer complex by an external excitation source the charge-transfer complex has a decaying time greater than 0.1 microsecond, preferably greater than one microsecond.

Another aspect of the invention refers to a security element, article or document which comprises a nanocompound as defined above, i.e. to a security element, article or document which comprises a charge-transfer complex of at least two different size metal atomic quantum clusters (AQCs), $M_n$ and $M'_{n'}$, of general formula (I):

$$M_n^+ M'_{n'}{}^- \qquad (I),$$

wherein
the metals, M and M', of the metal AQCs are the same or different metals,
$M_n$, is the smaller AQC which is present in its oxidized form, $M_n^+$,
$M'_{n'}$, is the larger AQC which is present in its reduced form, $M'_{n'}{}^-$,
$M_n^+$ and $M'_{n'}{}^-$ are bound by electrostatic interactions,
n and n' are respectively the number of metal atoms of M and M', and
n is smaller than n',
as defined above.

In one embodiment the security element is selected from substrate body, security threads, security fibers, watermarks, tactile effects, security cellulose strips, layers of glues, lacquers, plasters, planchettes, holograms, security inks and plastic sheets.

In another embodiment the security document or article is selected from security paper, envelopes, cheques, bank notes, identity documents, tickets, stamps, admission passes, impressed and certified papers.

In a further aspect, the present invention relates to a method for manufacturing a security element, document or article mentioned above, which comprises incorporating a charge-transfer complex of at least two different size metal atomic quantum clusters (AQCs), $M_n$ and $M'_{n'}$, of general formula (I):

$$M_n^+ M'_{n'}{}^- \qquad (I)$$

as defined above,
i) during the manufacturing of the material used to manufacture the security document or article,
ii) as part of an additive which is added to the security element, document or article,
iii) on the surface of said article or document, or
(iv) as part of one or more of the dyes or inks used in the manufacturing of the security document or article.

In another further aspect the invention relates to a method for determining the authenticity of a security document, article or element mentioned above which comprises:
(a) irradiating the security document, article or element with an external excitation source at a pre-determined excitation wavelength, $\lambda_{exc.}$ to excite the charge-transfer complex, and
(b) detecting one or more of the following parameters:
emission wavelength ($\lambda_{em.}$),
intensity,
mean lifetime,
anisotropy,
of said charge-transfer complex by suitable detection means.

In another aspect, the invention relates to a system for determining the authenticity of a security document, article or element as has been defined previously which comprises:
a positioner wherein the security document, article or element is placed;
means which allow focusing, transmitting and optionally amplifying the excitation originating from an external excitation source on the part of the document, article or element to be irradiated; and
suitable detection means for measuring one or more of the following parameters: emission wavelength ($\lambda_{em.}$), intensity, mean lifetime or anisotropy.

DETAILED DESCRIPTION OF THE INVENTION

The meanings of the terms of the present invention are detailed below.

The term "Atomic Quantum Cluster", abbreviated as AQC, is understood, as said before, as metal Atomic Quantum Cluster. Metal Atomic Quantum Clusters are formed exclusively by zero-oxidation-state metal atoms, in this invention preferably with equal or less than 309 metal atoms. The AQCs are stable over time. Preferably, the AQCs of the invention have sizes comprised between approximately 0.3 and 2.2 nm, preferably between approximately 0.3 and 2 nm, more preferably between approximately 0.3 and 1.8 nm. These metallic AQCs do not longer behave like a "metal" and their behaviour becomes molecular like. Therefore, new properties which are not observed in the nanoparticles, microparticles or metal materials in mass appear in these clusters. Therefore, the physical-chemical properties of the AQC cannot be simply extrapolated from those of the nano/microparticles.

The term "nanocompound" refers herein to a nanometric compound which comprises a charge-transfer complex of general formula (I):

$$M_n^+ M'_{n'}^- \qquad (I),$$

which may, optionally, have organic ligands attached to it. The outer diameter of the nanocompound is approximately equal to or less than 4 nm, preferably equal to or less than 3 nm, more preferably equal to or less than 2 nm. In another embodiment the outer diameter of the nanocompound is equal to or less than 1 nm or equal to or less than 0.6 nm.

The term "charge-transfer complex" also named CT complex, or CTC, or electron-donor-acceptor complex is herein understood as an association of at least two AQCs, in which a fraction of electronic charge, i.e. an electron, is transferred between the AQCs resulting in the formation of the oxidized form of one of the AQCs and the reduced form of the other AQC. The resulting electrostatic interaction, i.e. electrostatic attraction, provides a stabilizing force for the molecular complex. The source AQC from which the charge is transferred is called the electron donor and the receiving AQC is called the electron acceptor. In the present invention:

$M_n$ is the electron donor, which is the smaller AQC within the complex, and $M'_{n'}$ is the electron acceptor, which is the larger AQC within the complex.

The terms "smaller" and "larger" refers comparatively to the number of metal atoms, n and n', of each of the at least two AQCs present at the charge-transfer complex. Therefore, n is smaller than n' (n<n').

In a preferred embodiment, only one electron is transferred between the at least two AQCs, $M_n$ and $M'_{n'}$, therefore resulting the ionic forms, $M_n^+$, i.e. the oxidized form of $M_n$, and $M'_{n'}^-$, the reduced form of $M'_{n'}$, wherein "+" is a positive charge and "−" is a negative charge.

The letters "M" and "M'", in general formula (I), refer to the transition metal of the AQCs. As commented before, "M" and "M'" may be the same or different transition metal. Preferably the transition metal is selected from Au, Ag, Co, Cu, Pt, Fe, Cr, Pd, Ni, Rh and combinations thereof, preferably is selected from Au, Ag, Cu and combinations thereof, and more preferably it is selected from Au, Ag and combination thereof.

In the scope of this invention the term "combination of transition metals" refers to AQCs having atoms of at least two different transition metals as well as to the presence of AQCs of a single transition metal in the presence of AQCs of another transition metal different from the first such that the at least two AQCs of different size can be AQCs with the same transition metal, AQCs with different transition metal, or AQCs with the same or different bimetal combination.

The letters "n" and "n'" refer to the number of transition metal atoms of each AQC. As commented above n is smaller than n' (n<n'). Preferably, the minimum difference between n and n' is five metal atoms. In a preferred embodiment the difference between n and n' is between 5 and 50 atoms, in a particular embodiment the difference between n and n' is between 5 and 25 atoms and in another embodiment the difference between n and n' is between 5 and 15.

The "organic ligands" that may be attached to the charge-transfer complex are at least two different types of organic ligands, and preferably the at least two different types of organic ligands are selected from ω-hydroxyacid (HO—(CH$_2$)$_m$—COOH) and ω-mercaptoacid (HS—(CH$_2$)$_p$—COOH) ligands where m and p have a value between 2 and 30, preferably m and p have a value between 10 and 20. In a particular embodiment m and p have a value of 15. In another particular embodiment m and p have a value of 11. The value of m and p can be different or the same. In the event that m and p are different the difference between them is less than 6 carbons, preferably the difference of the values of m and p is between 1 and 4. In a preferred embodiment m and p are the same. Wherein the at least two different types of organic ligands are selected from ω-hydroxyacid (HO—(CH$_2$)$_m$—COOH) and ω-mercaptoacid (HS—(CH$_2$)$_p$—COOH) ligands, the acid groups, —COOH, (or —COO$^-$, if the salt of the corresponding acid is used) are directed towards the outer surface of the nanocompound and the —OH and —SH groups directed towards the inside, i.e. towards the ionized AQCs, $M_n^+$ and $M'_{n'}^-$, being bound, attached or coordinated to them.

In another embodiment the "organic ligands" that may be attached to the charge-transfer complex have other functional groups than hydroxyl, —OH, or mercapto, —SH groups, such as —NH$_2$, —NH—, —Cl, —PH$_3$, —SR, —OR, —NR$_2$, —NHR, —NR—, wherein R represents an organic group of a short hydrocarbon chain, C$_1$-C$_4$ capable of bound, attach or coordinate the AQCs or the ionized AQCs, $M_n^+$ and $M'_{n'}^-$. Is also possible exchanging the hydroxyl, —OH, or mercapto, —SH groups of the ω-hydroxyacid (HO—(CH$_2$)$_m$—COOH) and ω-mercaptoacid (HS—(CH$_2$)$_p$—COOH) ligands with these others, mentioned above that also interact with the metals of the AQCs.

In the context of the present invention, the luminescent nanocompounds, preferably the fluorescent nanocompounds, described present Stokes shifts greater than approximately 150 nm, preferably greater than approximately 300 nm.

There exist different methods for obtaining the nanocompounds of the invention for their use as markers for a security document, article or element.

One method comprises the step of preparing aqueous solutions of the AQCs, $M_n$ and $M'_{n'}$. Preferably both solutions have approximately the same concentration of AQCs, i.e. both solutions are equimolar or approximately equimolar. In a further step both solutions are mixed and stirred together to allow the charge-transfer mechanism to occur. In a preferred embodiment the reaction temperature is between 20° C. and 80° C. In another embodiment the reaction time is between 5 minutes and three hours.

Another method for obtaining the charge-transfer complexes used as markers for a security document, article or element, particularly the charge-transfer complex which additionally comprises organic ligands, wherein the organic ligands are amphiphilic molecules such as ω-hydroxyacids and ω-mercaptoacids attached to the atomic quantum clusters, $M_n$ and $M'_{n'}$, comprises the following steps:

a) preparing a nanosome by mixing ω-hydroxyacids and ω-mercaptoacids in the presence of a base in aqueous medium, b) adding at least one metal salt to the mixture prepared in step a), c) reducing the mixture obtained in step b), and d) breaking the nanosomes present in the mixture obtained in step c).

The term "nanosome" herein relates to a nanometric sized vesicle artificially prepared. Thus, the term "nanosome" refers to an spheroid nanometric supramolecular structure formed by one layer of amphiphilic molecules (for example lipids) having two hydrophilic groups bound each one at each end of the aliphatic $-(CH_2)_n-$ chain, or at the antepenultimate, $\chi$, penultimate, $\psi$, positions of the aliphatic $CH_3-(CH_2)_n-$ chain.

The amphiphilic molecules forming said monolayer in the nanosomes of the invention comprise:

a hydrophilic group such as carboxyl (COOH), carboxylate ($COO^-$) or phosphate ($PO_4^-$) group, for example, that are on the outer surface of the vesicle, at one end of the aliphatic chain and substituted at the antepenultimate, $\chi$, penultimate, $\psi$, positions of the aliphatic $CH_3-(CH_2)_n-$ chain, or last, $\omega$, positions of the aliphatic $-(CH_2)_n-$ chain with groups such as for example $-OH$, $-SH$, $-NH_2$, $-NH-$, $-Cl$, $-PH_3$, $-SR$, $-OR$, $-NR_2$, $-NHR$, or $-NR-$, wherein R represents an organic group of a short hydrocarbon chain, $C_1$-$C_4$, capable of forming nanosomes which are located towards the inside of the vesicle, at the other end of the aliphatic chain or at the ultimate positions of said aliphatic chain with respect to hydrophilic group, said groups forming the nanocavity with an inner diameter less than or equal to 10 nm, preferably less than or equal to approximately 5 nm, more preferably between 0.8 and 4 nm. In a particular embodiment, the inner diameter of the nanocavity is between approximately 1.5-1.8 nm.

Figure 1:
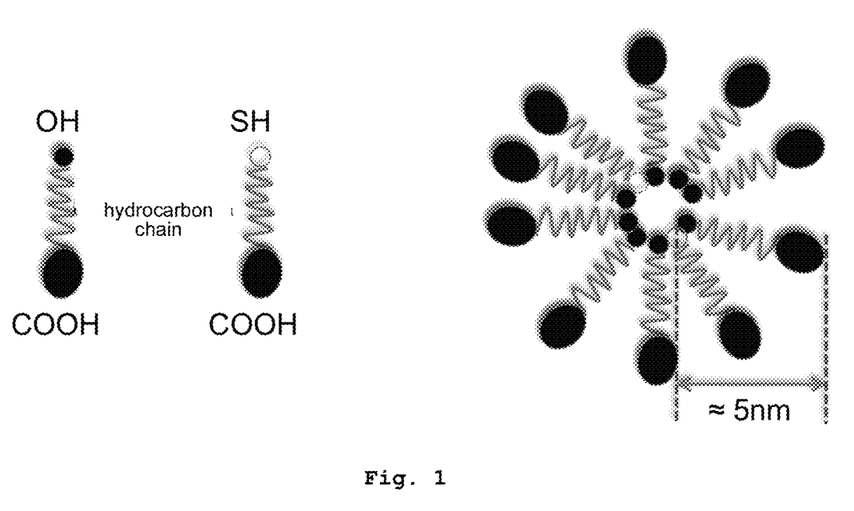
FIG. 1 shows a schematic depiction of a nanosome where the ω-hydroxyacids and ω-mercaptoacids form the monolayer of the nanosome wherein the monolayer has an approximate thickness of 5 nm, it is observed that the acid groups form the outer surface of the nanosome and the hydroxyl, OH, and mercapto, SH, groups face inwards forming the surface of the inner cavity of the nanosome.
Figure 2:
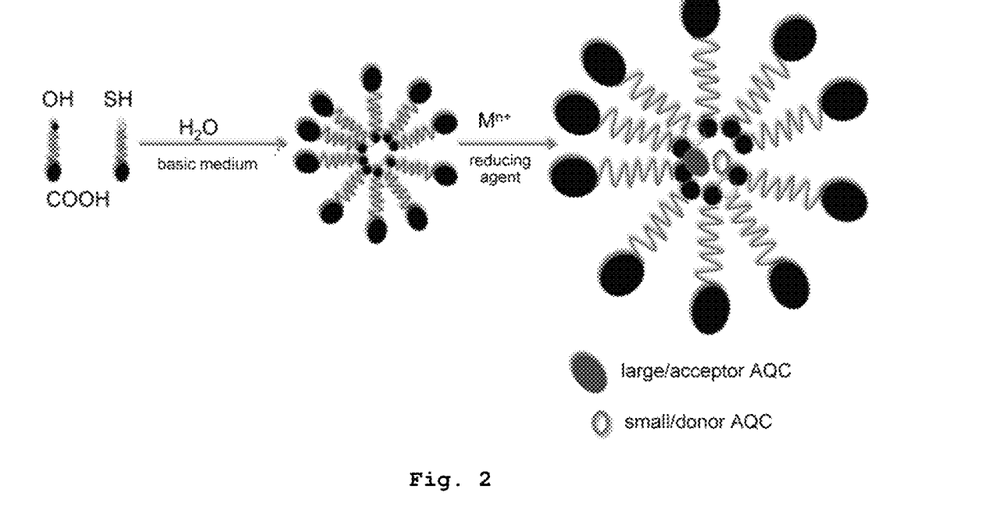
FIG. 2 shows a schematic depiction of the formation of the AQCs inside the nanosystem particularly inside the nanosomes.

In a preferred embodiment the term "nanosome" refers to a spheroid nanometric supramolecular structure formed by ω-hydroxyacids and ω-mercaptoacids. In this particular embodiment the nanosome comprises ω-hydroxyacids ($HO-(CH_2)_m-COOH$) and ω-mercaptoacids ($HS-(CH_2)_p-COOH$) as defined above (see FIG. 1). The ω-hydroxyacids and ω-mercaptoacids present in the nanosome are forming a spherical monolayer with the acid groups, $-COOH$, (or $-COO^-$, if the salt of the corresponding acid is used) directed towards the outer surface of the nanosystem, i.e. the nanosome, and the $-OH$ and $-SH$ groups directed towards the inside forming an inner cavity in the nanosome such that two approximately concentric spheres are formed, or as referred to in the literature, in the form of fatty acids "bola". This spherical monolayer can have a thickness between approximately 2-10 nm, preferably approximately 5 nm.

The inner cavity of the nanosome is closed. The inner diameter of said inner cavity is less than or equal to 10 nm, preferably less than or equal to approximately 5 nm and more preferably the inner diameter of said inner cavity is between approximately 0.8 and 4 nm. In a particular embodiment the diameter of this inner nanocavity is between approximately 1.5-1.8 nm. In this particular embodiment of the nanosomes, said nanocavity is formed by hydroxyl, $-OH$, and mercapto, $-SH$ groups, however exchanging these functional groups with others that also interact with the metals, such as $-NH_2$, $-NH-$, $-Cl$, $-PH_3$, $-SR$, $-OR$, $-NR_2$, $-NHR$, $-NR-$, where R represents an organic group of a short hydrocarbon chain, $C_1$-$C_4$ capable of forming nanosomes, is possible.

Tetrabutylammonium hydroxide, tetraoctylammonium hydroxide, triethylbenzylammonium hydroxide, tri-n-octylmethylammonium hydroxide, trimethyldecylammonium hydroxide, tetramethylammonium hydroxide, tetraethylammonium hydroxide or any other hydroxide having a voluminous group such as a counterion, preferably tetrabutylammonium hydroxide can be used as a base in the step a) of preparing a nanosome by mixing ω-hydroxyacids and ω-mercaptoacids.

In step b) metal salts of transition metals or combinations thereof can be used. Non limiting examples of metal salts are nitrates, sulfates, sulfites, chlorides, bromides, iodides, phosphates, hydroxides, cyanates, carboxylates, thiomalates, thioglucosates of the transition metals. Examples of these metal salts to be used as a single metal salt or in combination with other metal salts are $AgNO_3$, $CH_3COOAg$, $Ag_3AsO_4$, $AgBrO_3$, $AgBr$, $Ag_2CO_3$, $AgClO_3$, $AgCl$, $AgCrO_4$, $AgOCN$, $AgIO_3$, $AgI$, $Ag_2O$, $AgClO_4$, $Ag_3PO_4$, $Ag_2SO_4$, $Ag_2S$, $Ag_2SO_3$, $CuSO_4$, $CuCl_2$, $CuBr_2$, $CuI_2$, $Cu_2S$, $CuSCN$, $CuCN$, $CuCO_3$, $Cu_2O$, $Cu(OH)_2$, $Cu(NO_3)_2$, $Cu(ClO_4)_2$, $Cu(HCO_2)_2$ or $Cu(CO_2CH_3)_2$. Non-limiting examples of gold metal salts to be used in combination, are $HAuCl_4$, $AuCl$, $AuCl_3$, $HAuCl_4$, $HAuCl_4.aq$, $KAuCl_4$, $LiAuCl_4$, $(CH_3)_2SAuCl$, $C_3H_9AuClP$, $C_6H_{15}AuClP$, $C_{18}H_{15}AuClP$, $C_8H_{11}AuClP$, $C_5H_5AuCl_3N$, $(C_4H_9)_3PAuCl$, $C_{27}H_{36}AuClN_2$, $C_{21}H_{12}AuClF_9P$, $C_{20}H_{27}AuClP$, $C_{33}H_{49}AuClP$, $C_{42}H_{63}AuClO_3P$, $C_{21}H_{24}AuClN_2$, $C_{35}H_{49}AuF_6NO_4PS_2$ or $(C_{20}H_{15}AuF_6NO_4PS_2).2C_7H_8$.

Non-limiting examples of reduction systems or reducing agents to be used in step c) for reducing the mixture obtained in step c) can be $NaBH_4$, DIBAH, LiAlH4, $N_2H_4$ or $SnCl_2$ and also gentler reducing agents such as sodium hypophosphite, amines, sugars, organic acids, polymers such as polyvinylpyrrolidone, UV-VIS radiation, ultrasounds and photoreduction.

After the steps b) and c) of the present method, "nanosomes comprising AQCs" are formed. These "nanosomes comprising AQCs" comprise inside their inner cavity, i.e. encapsulated, the AQCs of at least two different sizes, i.e. $M_n$ and $M'_{n'}$.

A particular example of these "nanosomes comprising AQCs" is described in Gaillard, C., *Journal of Colloid and Interface Science*, Vol. 337, 2, 610-613, which describes gold particle synthesis inside these nanosystems.

The step of breaking down the nanosomes is a desestabilization process of the previously synthesized nanosomes. This step may be accomplished by different mechanisms. In a preferred embodiment the step of breaking the nanosomes, or destabilize the nanosomes, is made by means of ultracentrifugation, but any other means known in the art may be also useful for breaking the nanosomes, such as a thermal treatment or pH variation. The charge-transfer mechanism takes place during the step of breaking down the nanosomes. The nanosome is therefore destabilized and the charge-transfer complex of general formula (I) is formed.

It is also possible to obtain the charge-transfer complex used as markers for a security document, article or element by breaking other nanosystems other than nanosomes which comprise in their inner cavities AQCs of at least two different sizes, i.e. $M_n$ and $M'_{n'}$.

The term "nanosystem" refers to an spheroid-like nanometric supramolecular structure formed by one or two layers of amphiphilic molecules, wherein said amphiphilic molecules form a nanocavity at the inside of the nanosystem. Particularly, the nanosystem having an outer diameter approximately equal to or less than 20 nm, preferably equal to or less than 18 nm and more preferably equal to or less than 15 nm. The inside of the nanosystem comprised at least one nanocavity with an inner diameter less than or equal to 10 nm, preferably less than or equal to approximately 5 nm, more preferably between 0.8 and 4 nm. In a particular embodiment, the inner diameter of the nanocavity is between approximately 1.5-1.8 nm. Non-limiting examples of nanosystems are nanosomes but also micelles, reverse micelles, nanoemulsions or microemulsions. In a preferred embodiment the nanosystem is a nanosome.

The expression "spheroid-like" means that it has a solid geometrical figure similar in shape to a sphere.

The amphiphilic molecules forming the nanosystems may be the same or different, preferably two different type of molecules, and each molecule possess both hydrophilic and lipophilic properties.

The lipophilic properties are given by a group which is typically a hydrocarbon moiety, such as an aliphatic chain of the form $CH_3-(CH_2)_n-$ or $-(CH_2)_n-$ being 30>n>2, preferably 20>n>10.

The hydrophilic properties are given by a hydrophilic group. The hydrophilic group may be a charged group or a polar uncharged group. The charged group is selected from anionic groups, preferably is selected from the group formed by carboxylates, sulfates, sulfonates and phosphates. The polar uncharged group is selected from the group formed by —OH, —SH, —$NH_2$, —NH—, —Cl, —$PH_3$, —SR, —OR, —$NR_2$, —NHR and —NR—, wherein R represents an organic alkyl group of a short hydrocarbon chain, $C_1$-$C_4$, preferably methyl, ethyl or propyl group.

The amphiphilic molecules may have one aliphatic $CH_3$—$(CH_2)_n$— chain and one hydrophilic group bound to it or two hydrophilic groups bound each one at each end of the aliphatic —$(CH_2)_n$— chain.

The term "micelle" refers to amphiphilic molecules aggregates. In an aqueous medium, the lipophilic domains of the molecule aggregate are oriented towards the inside of the micelle and the hydrophilic domains are in contact with the medium. In "reverse micelles" the molecules are organized such that the lipophilic region is exposed to the outside and the hydrophilic region to the inside. In the state of the art the term "microemulsion" is also used to refer to a "reverse micelle", i.e. the "microemulsion" is a particular embodiment of a "reverse micelle". The term "microemulsion" refers to a system of at least three components (water, organic solvent-known commonly as oil- and amphiphilic compound), single phase and thermodynamically stable, formed by nanometric sized droplets. Although not restrictive, the use of water-in-oil microemulsions wherein water droplets are dispersed in the organic medium is of particular interest for the present invention. Among these water-in-oil microemulsions, the use of polymerized microemulsions relating to microemulsions containing acrylic monomers, for example acrylamide or 1,6-hexanediol diacrylate inside the water droplets which are polymerized by means of introducing some initiator, such as for example a radical photoinitiator, is also of interest due to its stability. Thus, the microemulsion droplets can become more resistant.

The term "nanoemulsion" refers to a system of at least three components (water, organic solvent and stabilizing compound), two-phase and thermodynamically unstable but is temporary stabilized by chemical or physical processes and is formed by nanometric droplets. The formation of nanometric droplets is the only thing that differentiates the nanoemulsions from the emulsions known in the state of the art, therefore the term "nanoemulsion" generally refers to an emulsion in which the droplets are of nanometric size.

In a particular embodiment the nanosystem is selected from the group formed by nanosome, micelle and reverse micelle, preferably the nanosystem is a nanosome.

In the particular embodiment wherein the nanosystem is a reverse micelle, the reverse micelle comprises at least two different surfactants, wherein at least one comprises a thiol or thioether group as its polar group. In a more particular embodiment, the at least two surfactants are an alcohol ethoxylate and a ω-mercaptoacid.

The inner cavity of the nanosystem is closed. As mentioned above, the inner diameter of said inner cavity is less than or equal to 10 nm, preferably less than or equal to approximately 5 nm and more preferably the inner diameter of said inner cavity is between approximately 0.8 and 4 nm. In a particular embodiment the diameter of this inner nanocavity is between approximately 1.5-1.8 nm.

An approximate estimation of the cluster excitation and emission wavelengths can be determined by approximation by means of the Jellium model (see J. Calvo et al., *Encyclopedia of Nanotechnology*, Ed. by B. Bhushan, Springer Verlag, 2011, for example). This model predicts in a rather approximate manner the prohibited energy bandgap of the clusters and, therefore, the position of the emission bandgap thereof. The excitation bandgap of the clusters can in turn be predicted from the emission bandgap taking into account that the Stokes shift in clusters of a particular size is of approximate 50-100 nm. The following table, Table 1, shows the theoretical data for AQCs of Au or Ag according to this mode, i.e., the approximate excitation $\lambda_{exc.}$, and emission, $\lambda_{em.}$, wavelengths have been calculated with an error of ±50 nm in AQCs of Au or Ag by means of said Jellium model: $E_{em}=E_F/N^{1/3}$; where $E_{em}$=emission energy; N=no. of atoms in the AQC; and $E_F$=Fermi level which is the same approximately 5.5 eV for gold and silver.

TABLE 1

| Cluster | $\lambda_{exc.}$ (nm) | $\lambda_{em.}$ (nm) |
|---------|-----------------------|----------------------|
| $A_2$ | 200-250 | 300 |
| $A_3$ | 240-290 | 340 |
| $A_4$ | 270-320 | 370 |
| $A_5$ | 300-350 | 400 |
| $A_6$ | 325-375 | 425 |
| $A_7$ | 350-400 | 450 |
| $A_{10}$ | 400-450 | 500 |
| $A_{12}$ | 440-490 | 540 |
| $A_{15}$ | 475-525 | 575 |
| $A_{20}$ | 535-585 | 635 |
| $A_{25}$ | 580-630 | 680 |
| $A_{30}$ | 630-680 | 730 |
| $A_{40}$ | 700-750 | 800 |

These values can also vary in practice when the nanosystem is made to react to exchange the OH and SH groups with other ligands in the inner cavity of the nanosystem. Without being limiting, the ligands to be exchanged can be chosen from —$NH_2$, —NH—, —Cl, —$PH_3$, —SR, —OR, —$NR_2$, —NHR, —NR—, where R represents a short chain organic group capable of forming nanosomes.

In other words, the type of clusters to be used to obtain a particular excitation and emission wavelength can be decided from the table above. Thus, for example, to obtain a system with an excitation wavelength at 300 nm, an emission wavelength at 600 nm and a Stokes shift of 300 nm, the following cluster sizes should be selected:

excitation cluster ("donor", $M_n$): $M_3/M_5$, emission cluster ("acceptor", $M'_{n'}$): $M'_{12}/M'_{20}$.

Figure 6:
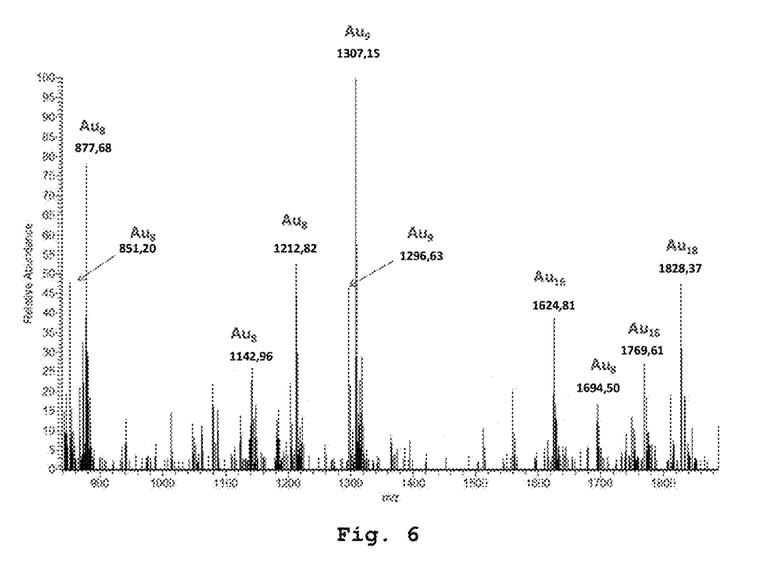
FIG. 6 shows the ESI-orbitrap mass spectrum for the charge-transfer complex obtained in Example 1.

This was experimentally confirmed for the Example 1, by mass spectrometry (FIG. 6 where signals for $Au_8/Au_9$ and $Au_{18}/Au_{20}$ were found, both near the range of the predicted AQCs.

Documents, Articles and Elements of Security

In an additional aspect, the present invention relates to a security element which comprises a nanocompound as defined above, i.e. to a security element, article or document which comprises a charge-transfer complex of at least two different size metal atomic quantum clusters (AQCs), $M_n$ and $M'_{n'}$, of general formula (I):

$$M_n^+ M'_{n'}{}^-  \qquad (I),$$

wherein the metals, M and M', of the metal AQCs are the same or different metals, $M_n$, is the smaller AQC which is present in its oxidized form, $M_n^+$, $M'_{n'}$, is the larger AQC which is present in its reduced form, $M'_{n'}{}^-$, $M_n^+$ and $M'_{n'}{}^-$ are bound by electrostatic interactions, n and n' are respectively the number of metal atoms of M and M', and n is smaller than n', as defined above.

According to the present invention, the term security element relates to an element which is integrated into a security document or article for the purpose of authenticating it. The security element can be integrated into the security article or document in its body, such as for example in the substrate body, security threads, security fibers, watermarks, tactile effects, cellulose strips, layers of glues, lacquers, plasters, planchettes or other commonly used elements, or on its surface, such as for example holograms added in different bills and credit cards, security inks, plastic sheets or other commonly used elements.

In the scope of the present invention, "substrate" is understood as paper, polymer or polymer combination.

The security element can be randomly distributed or attached in specific positions of the document or article and gives security features to the document or article containing it, these features being able to be of a very diverse kind provided that their objective is to make the forging of the security documents or articles difficult or to facilitate the authentication thereof.

According to a particular embodiment, the security element is selected, for example from substrate body, security paper, security threads, security fibers, security inks, watermarks, tactile effects, cellulose strips, planchettes, holograms, security pigments or substances, and sheets. These security elements can be prepared incorporating the nanocompounds or from the security compositions comprising the nanocompounds by following the common methods known by the person skilled in the art.

In a particular embodiment of the invention, the nanocompounds are deposited in supports with the form of fibers. Thus, it is possible to deposit said nanocompounds on natural fibers, preferably cotton fibers, such that security fibers which are incorporated into the security element as part of the fibers themselves which form the security paper is provided.

In another particular embodiment, the luminescent nanocompounds used in the invention are deposited on support particles which in turn are incorporated into the formulation of an ink thus giving rise to security inks. In another embodiment, the nanocompounds are directly incorporated into the formulation of an ink.

In a particular embodiment, the security element is formed by a security composition comprising a type of luminescent nanocompound used in the present invention, in another particular embodiment the security element is formed by a security composition comprising the combination of at least two types of luminescent nanocompounds used in the present invention. In another particular embodiment, the security element is formed by the combination of at least two security compositions wherein each of said security compositions comprises one type of luminescent nanocompounds used in the present invention as has been defined previously.

In another particular embodiment, the security element is formed by the combination of two security inks wherein each of said security inks comprises one type of luminescent nanocompounds used in the present invention as has been defined previously. In this embodiment, the types of nanocompounds comprised in both security inks have the same chemical composition but they have different AQCs size, i.e., they have different Stokes shift.

In another particular embodiment, the security element is formed by the combination of two security inks wherein each of said security inks comprises one type of luminescent nanocompounds used in the present invention as has been defined previously. In this embodiment, the types of nanocompounds comprised in both security inks have different chemical composition since the metals of the AQCs are different.

In the particular case of using inks, the security element is not only formed by a material with well defined properties in terms that it presents a specific Stokes shift, emission wavelength ($\lambda_{em}$), intensity, mean lifetime or anisotropy, rather also by a particular code, either a two dimensional image, an anagram or a binary code such as a barcode. This method simplifies the detection of the security element since the latter is located in a well defined region of the security document.

Additionally, these security elements can be used as markers for security articles or documents.

In another aspect, the invention also relates to a security article or document comprising the luminescent nanocompounds used in the present invention as has been defined previously. Likewise, the invention relates to a security article or document comprising a security element as has been described previously.

According to the present invention, the term security article or document relates to those having particular characteristics which ensure their origin and therefore their authenticity. These security articles or documents include all of those used by public administrations and their public organizations as well as those used in the private sector when they circulate greatly between the group of citizens and companies, and containing identification, authentication or anti-forgery means or devices. Preferably, the security documents or articles are selected from identification documents such as identification cards, passports, passes and the like, and valuable documents such as bills, cheques, stamps, certificates and the like.

Preferably, the security article or document is selected from security paper, identification documents, banknotes, cheques, stamps and stamp-impressed paper, labels and tickets. More preferably, it is a security paper.

The luminescent nanocompounds used in the invention can be incorporated into the security article or document:

(i) during the manufacturing of the material used to make said article or document;

(ii) as part of an additive which is added to said article or document;

(iii) on the surface of said article or document; or (iv) as a part of one or more of the dyes or inks used in the manufacturing of the security document or article.

In a particular embodiment, the luminescent nanocompounds used in the invention can form part of a single security composition which is incorporated into the security article or document according to any one of method i)-iv) described previously.

The luminescent nanocompounds used in the present invention can be added to the body of paper of the security documents as a dispersion forming part of the substrate body itself. Nevertheless, the incorporation thereof on the surface of the document as a hologram or as an inscribed security thread, or forming part of the glue or lacquer, is preferred. It can also be incorporated into polymer films such as polyvinyl alcohol films, for example, which can coat the security article or document. Likewise, the luminescent nanocompounds can be incorporated into inks used for printing the security document, enabling forming imperceptible part of images, figures, legends, barcodes or elements for tactile labeling.

The functionalization of the nanocompounds on microparticles further allows solving the problem where the nanocompounds pass through the pores of the section of the substrate since the microparticles are retained in the substrate body due to their large size.

Thus, the sizes of nanocompounds defined in the invention guarantee its incorporation and stay in the substrate preferably in the paper. Thus, the security document or article is provided with the code corresponding to the combination of selected luminescent nanocompounds.

In a particular embodiment of the invention, the luminescent nanocompounds are deposited in substrates with the form of fibers. Thus, it is possible to deposit said nanocompounds on natural fibers, preferably cotton fibers, such that security fibers are directly incorporated into the security material as part of the fibers themselves which form the paper is provided.

In another particular embodiment, the luminescent nanocompounds are deposited on microparticles where the latter in turn are incorporated into the substrate body or are incorporated into the formulation of the ink itself, thus forming security inks as has been mentioned previously for the security elements.

In a particular embodiment, the percentage of the luminescent nanocompounds of the invention incorporated into the security document, article or element is less than 5% by weight, preferably less than 1% by weight, and greater than 0.001% by weight of the total weight of the security document or article. This low concentration makes the compositional identification by techniques used such as chemical analysis, X-ray diffraction, spectroscopic techniques or the like difficult. Nevertheless, the identification of the composition does not represent the security marker therein since the specific response is achieved by the external excitation of the luminescent nanocompounds by measuring the emission transmitted by said nanosystems after said excitation or by measuring any other parameters characteristics of the luminescent nanocompounds of the invention.

The number of different security markers increases with the number of different AQC sizes, transition metals and the combination thereof used which are characterized by their chemical composition as well as by the size of the nanocompounds, therefore, the number of different security markers that can be generated is virtually limitless. This allows generating encoded security markers such that a particular security marker corresponds to the documents that have been created at a particular time, or for a particular value or a particular purpose, or by a particular organism, therefore making the security documents traceable and further increasing the security thereof.

The security compositions comprising the luminescent nanocompounds of the invention are always active, a security composition not showing luminescence after the application of an external excitation not being possible. Thus, it is impossible that a security document can be falsified by not having the features corresponding to the security composition. Likewise, the luminescence response of the materials comprised in the security compositions cannot be modified without the security document which the materials form a insoluble part being destroyed, therefore the security compositions are characterized by being permanent and non deactivable.

The luminescent nanocompounds used in the invention are formed by very stable materials, not being sensitive generally to oxidation or hydration processes. Nevertheless, the nanocompounds can sometimes be coated with layers of inert materials such as alumina, glasses, silicates, or other oxide materials for protecting them from the environment. In the same manner, the nanocompounds could also be coated with polymers or other organic materials to improve their adherence to the fibers of the paper or for their improved transmission in the event that they form part of inks.

The combination of the luminescent nanocompounds of the invention described in the present invention allows efficiently labeling the security articles or documents, presenting a safe coding system. The security compositions described are permanent, non deactivable and have an encoded response which requires the use of a detection system designed for such purpose.

Authentication Method

In another aspect, the invention relates to a method for determining the authenticity of a security document or article which comprises measuring the luminescence of said security document or article to determine the presence of the security marker, i.e., to determine the presence of the nanocompounds presenting luminescence, preferably fluorescence.

In a particular embodiment, there is no blinking or photobleaching for at least 500 minutes exciting the samples at 300 nm every 30 seconds.

In a particular embodiment, the emission lifetime ($\tau$) can be measured. The emission lifetime ($\tau$) which is the luminescence extinction time or the mean lifetime which is the time lapsed since the end of the excitation until the emission intensity reduces to 1/e of the maximum intensity value, i.e., until it reduces to approximately 37%. In an embodiment of the present invention the mean lifetime of the luminescence, preferably fluorescence, is greater than 0.1 µs, preferably greater than 1 µs. In a particular embodiment, the nanocompounds synthesized have an emission lifetime greater than microsecond for more than 37% of the fluorescence signal.

In a particular embodiment, the invention relates to a method for determining the authenticity of a security document or article comprising at least one nanocompound of the invention which comprises:
  (a) irradiating the security document or article with one or several external excitation source; and
  (b) detecting one or more of the following parameters:
     emission wavelength ($\lambda_{em.}$),
     intensity,
     mean lifetime,
     anisotropy,
  of said at least one nanocompound by suitable detection means.

The "external excitation source" can be any class of pulsed or continuous intense radiation source, for example light emitting diodes, laser diodes, giant pulse lasers and light sources derived from the same by means of nonlinear optics as well as X-ray pulses or particle beams, particularly pulsed electron beams.

Therefore, in a particular embodiment, the method for determining the authenticity of a security document or article as has been defined previously comprises:
- a) irradiating the security document or article with an external radiation source;
- b) detecting one or more of the following parameters:
    - emission wavelength ($\lambda_{em.}$),
    - intensity,
    - mean lifetime,
    - anisotropy, Of said at least one nanocompound by suitable detection means;

and optionally,
- c) comparing the emission wavelength obtained, the intensity, the mean lifetime or the anisotropy obtained in step b) with a value of the emission wavelength, intensity, mean lifetime or reference anisotropy corresponding to a security document or article comprising the luminescent nanocompound.

The authenticity of the security document or article is confirmed in step c) after verifying whether the value of the parameters obtained in step b) coincides with the reference parameters of the security marker, or whether it is within the pre-established limits.

According to another particular embodiment, the emission wavelength, the intensity, the mean lifetime or the anisotropy obtained after impacting the external radiation on the security document or article represents a codification.

Detector

In a particular embodiment, the system for determining the authenticity of a security document, article or element as have been defined previously comprises:
- a positioner wherein the security document, article or element is placed;
- means which allow focusing, transmitting and optionally amplifying the excitation originating from an external excitation source on the part of the document, article or element to be irradiated; and
- detection means suitable for measuring one or more of the following parameters: emission wavelength ($\lambda_{em.}$), intensity, mean lifetime or anisotropy.

In a preferred embodiment the method for detecting the nanocompound additionally comprises in the step for detecting one or more of the following parameters, emission wavelength, $\lambda_{em.}$ intensity, mean lifetime or anisotropy, is performed with a particular delayed time. This embodiment is based on the fact that the mean lifetime of the luminescence of the nanocompound of the invention are greater than 0.1 µs. The delayed time for detecting and measuring one or more of the parameters is greater than 0.1 µs and is preferably greater than 1 µs. Thus, possible interferences due to other emission wavelengths, $\lambda_{em}$, which can be created after excitation with an external excitation source at an excitation wavelength, $\lambda_{exc.}$, in addition to the emission wavelength of the nanocompound used in the present invention, are prevented.

"Exciting" is understood in the scope of the present invention as irradiating the nanocompound with a light radiation of a particular wavelength.

The "suitable detection means" relate to methods for detecting and optionally measuring the indicated parameters known by the person skilled in the art, i.e., methods for detecting the emission wavelength of the luminescence, particularly of the fluorescence, methods for detecting the intensity of the luminescence particularly of the fluorescence, methods for detecting the mean lifetime of the intensity of the luminescence or methods for detecting the anisotropy.

In another particular embodiment, this system further comprises a device which allows comparing the parameters obtained with reference parameters and thus verifying if the analyzed document, article or element comprises the security marker.

As used herein, the term "approximately" means a slight variation from the specified value, preferably within 10 percent of the specified value. However, the term "approximately" may mean a greater variation tolerance depending on, for example, the experimental technique used. The person skilled in the art understands said variations of a specified value and they are within the context of the present invention. Furthermore, in order to provide a more precise description, some of the quantitative expressions provided in the present document are not described with the term "approximately". It is understood that, the term "approximately" explicitly used or otherwise, each amount given in the present document attempts to refer to the actual given value, and it also attempts to refer to the approximation of such given value which would be reasonably deduced based on the common knowledge in the art, including equivalents and approximations due to experimental conditions and/or from measurement for such given value.

EXAMPLES

Example 1

Synthesis of $Au_{3-5}$—$Au_{15}$ Charge-Transfer Complex

Firstly, stock solutions of 12-mercaptododecanoic acid and 12-hydroxydodecanoic acid are prepared at a concentration of 10 mg/ml, a given volume of tetrabutyl ammonium hydroxide solution (1.5 M in water) is added to ensure a molar ratio of fatty acid/TBAOH of 1. Then nanosomes are prepared mixing a given volume of each fatty acid stock solution with 25 ml of pure water (3.6 ml of 12-mercaptododecanoic acid and 10 ml of 12-hydroxydodecanoic acid).

In a second step, a stock solution of 0.0147 M $HAuCl_4$ is prepared in pure water. Then 2.7 ml of this solution is poured in the nanosome sample. An extra amount of TBAOH solution is added to the mixture to ensure redispersion of the material. Then, 2.7 ml of a freshly prepared stock solution of 0.05 M $NaBH_4$ is added to the sample dropwise under vigorous agitation. The reaction is finished after 1 hour stirring at 35° C. in a thermostatted bath.

Then, a solution of the Au AQCs nanosomes obtained before was ultracentrifugated during one hour at 90000 rpm, obtaining the $Au_{3-5}$—$Au_{15}$ charge-transfer complex as the supernatant of the separation.

Figure 5:
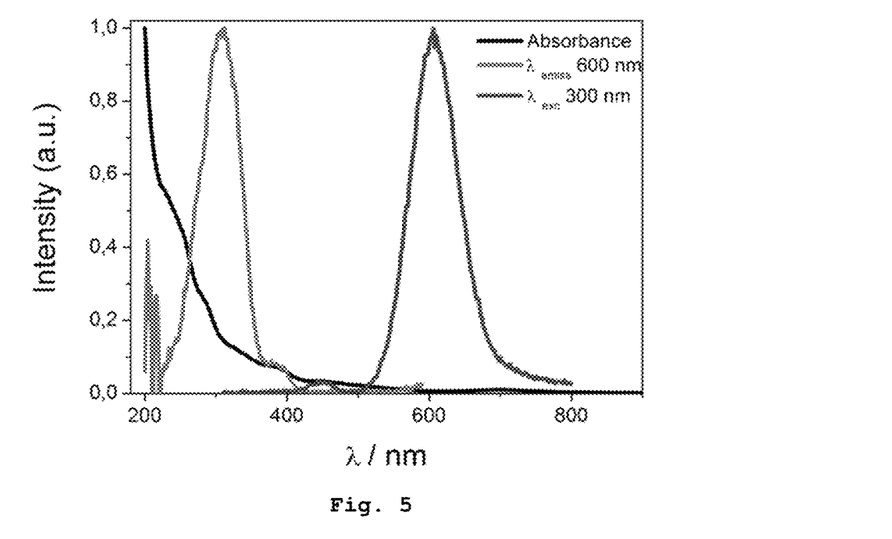
FIG. 5 shows the optic properties of the charge-transfer complex obtained in Example 1.

The fluorescent properties of $Au_{3-5}$—$Au_{15}$ charge-transfer complex are shown in FIG. 5, showing a Stokes shift of 320 nm.

Example 2

Synthesis of $Au_{13}$—$Au_{25}$ Charge-Transfer Complex

Figure 3:
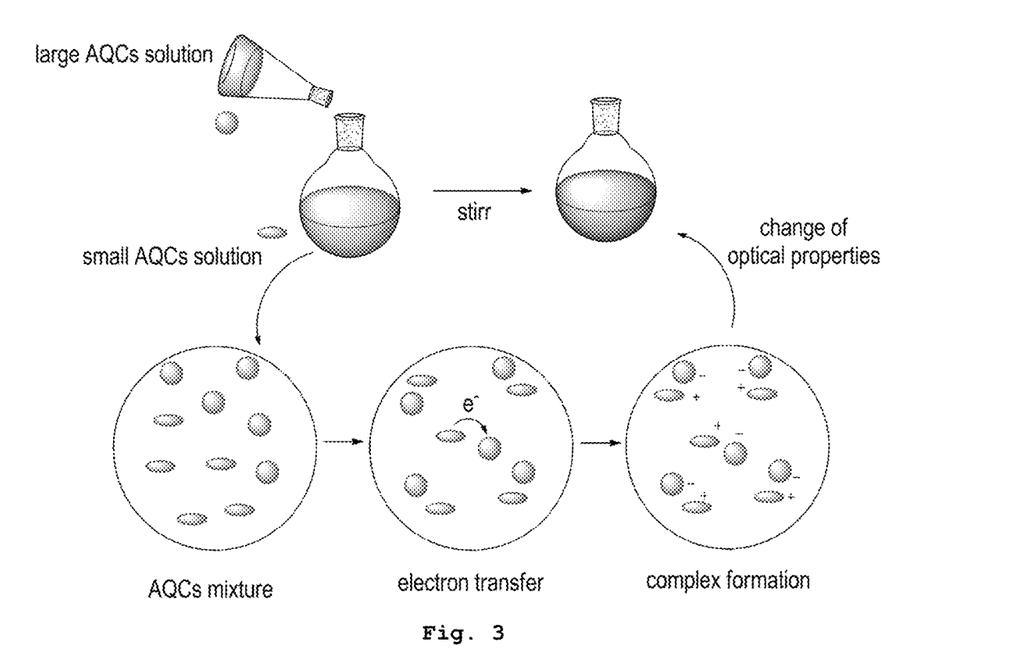
FIG. 3 shows the method for obtaining a charge-transfer complex without ligands attached to it and the charge-transfer mechanism.
Figure 4:
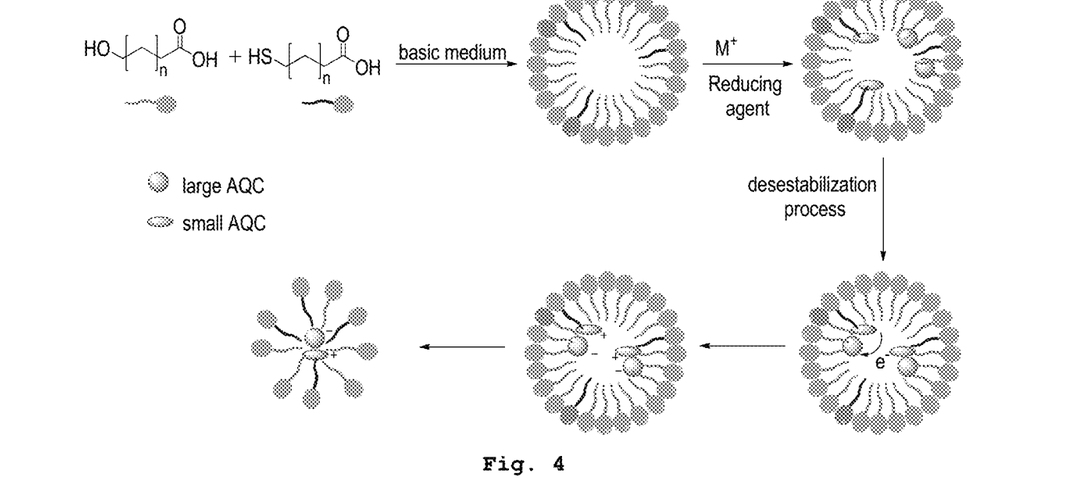
FIG. 4 shows the method for obtaining a charge-transfer complex with ligands attached to it and the charge-transfer mechanism.

Mix and stir overnight equivalent volumes of two equimolar, $Au_{13}$ and $Au_{25}$, aqueous AQCs solutions (0.1 mM en water), as shown in FIG. 3.

Examples of the synthesis of $Au_{13}$ and $Au_{25}$ AQCs are found, for example in Abad, J. M. et al., J. Am. Chem. Soc. 2007, 129 (43), 12932-12933; and Shichibu, Y. et al., J. Am. Chem. Soc. 2005, 127 (39), 13464-13465.

Example 3

Use of $Au_{3-5}$—$Au_{15}$ Charge-Transfer Complexes as Security Markers Applied on the Surface in Security Paper for Printing Legal Tender Notes This example uses a gravure printing machine manufactured by Panday-Graph, a gravure cylinder manufactured by Ziraba, natural cellular-based fibrous paper manufactured in a round paper machine in the Fábrica Nacional de Moneda y Timbre (FNMT), long-lasting varnish and crosslinker manufactured by Sicpa and a aqueous solution of $Au_{3-5}$—$Au_{15}$ charge-transfer complexes obtained in Example 1.

The main characteristics of the installations and materials indicated are described below:

Conditions of the Printing Machine on Each Side of the Paper:
Drying tunnel temperature: 145° C.
Machine speed: 90 m/min
Suction speed: 2500 rpm
Blowing speed: 2400 rpm
Residual moisture of the paper after drying: 6.1-6.8%
Conditions of the Gravure Cylinder
Type of etching: chemical
Lineature: 60 line/cm
Cell depth: 54 microns
Table: 910 mm
Diameter: 200 mm
Conditions of the Varnish and Crosslinker
Commercial name of the varnish: Primer 803696W
Commercial name of the crosslinker: First additive 370010
Viscosity of the varnish after adding crosslinker: 20 s CP4
Viscosity of the varnish for application: 18 s CP4
Main Conditions of the Paper:
Fibrous composition: 100% cellulose
Grammage: 90 g/m$^2$
Grammage after the varnishing process: 96 g/m$^2$
Thickness: 115 microns
Bendtsen smoothness on the felt side: <700 ml/min
Bendtsen smoothness on the fabric side: <800 ml/min
Bendtsen porosity: <20 ml/min
Bendtsen porosity after creasing: <140 ml/min
Cobb value: 40-70 g/cm$^2$
Ash: <3%
Opacity: 84%
Implementation Method:

Once the printing machine is started up to reach the established machine conditions, the gravure cylinder is placed, the reel of paper is placed on the unwinding screw and the web of paper is distributed in the machine circuit, the varnish is mixed with the crosslinker in a proportion of 1.5% by weight of the latter over the former, under gentle stirring conditions in the actual 20 kg drum of varnish. 100 ml of the aqueous solution of $Au_{3-5}$—$Au_{15}$ charge-transfer complexes obtained in Example 1 are added to this mixture. Once the perfect dispersion of the components is assured, the content of the drum is pumped to the inkwell of the printing machine. The paper is positioned on the printing cylinder starting the application of the varnish on the entire width of the web of paper on one of the sides, controlling the final moisture of the paper, viscosity of the varnish and the machine conditions throughout the entire printing process. Once the paper is wound at the machine outlet, the reel is taken off the winder and is placed in the unwinder in the appropriate unwinding direction to print the varnish on the opposite side. After the process ends the reel is left at rest for a minimum development time of 24 hours at room temperature (23° C. and 50% RH).

Example 4

Use of Nanosystems of Two $Au_{3-5}$—$Au_{15}$ Charge-Transfer Complexes Encapsulated in Nanosomes as Security Markers Applied in Silk-Screen Printing Ink with an Iridescent Web in Security Paper for Security Labels This example uses a silk-screen printing machine manufactured by Stork, a silk screen manufactured by Stork, natural cellular-based fibrous paper manufactured in a round paper machine in the FNMT, iridescent ink, anti-foaming agent and crosslinker manufactured by Sicpa and a dispersion of fluorescent AQC aqueous solution of $Au_{3-5}$—$Au_{15}$ charge-transfer complexes obtained in Example 1.

The main characteristics of the installations and materials indicated are described below:

Conditions of the Printing Machine on Each Side of the Paper:
Drying tunnel temperature: 145° C.
Machine speed: 70 m/min
Suction speed: 2500 rpm
Blowing speed: 2400 rpm
Residual moisture of the paper after drying: 6.5%
Conditions of the Silk Screen
Reference: RSI900
Development: 25⅜"
Mesh: 105
Open area: 15%
Thickness: 105 microns
Width: 910 mm
Conditions of the Iridescent Ink and Additives:
Commercial name of the ink: Silk-screen printing ink 5WR1241
Commercial name of the anti-foaming agent: Additive 880775
Commercial name of the crosslinker: Additive 370010
Viscosity of the ink after adding crosslinker: 20 s CP4
Viscosity of the printing ink: 18 s CP4
Main Conditions of the Paper:
Fibrous composition: 100% cotton cellulose
Grammage: 90 g/m$^2$
Grammage after the varnishing process: 96 g/m$^2$
Thickness: 115 microns
Bendtsen smoothness on the felt side: <700 ml/min
Bendtsen smoothness on the fabric side: <800 ml/min
Bendtsen porosity: <20 ml/min
Bendtsen porosity after creasing: <140 ml/min
Cobb value: 40-70 g/cm$^2$
Ash: <3%
Opacity: 84%
Implementation Method:

Once the printing machine is started up to reach the established machine conditions, the silk screen is placed, the reel of paper is placed on the unwinding screw and the web of paper is distributed in the machine circuit, the ink is mixed with the crosslinker in a proportion of 1.5% by weight of the latter over the former, under gentle stirring conditions in the actual 20 kg drum of ink. 100 ml of the aqueous solution of $Au_{3-5}$—$Au_{15}$ charge-transfer complexes obtained in Example 1 and anti-foaming agent are added to this mixture as needed should foam occur. Once the perfect dispersion of the components is assured, the content of the drum is pumped to the inkwell of the printing machine. The paper is positioned on the printing silk screen starting the printing of the ink through the holes of the screen according to the graphic design established therein on one of the sides, controlling the final moisture of the paper, viscosity of the ink and the machine conditions throughout the entire printing process.

Example 5

Use of $Au_{3-5}$—$Au_{15}$ Charge-Transfer Complexes Encapsulated in Nanosomes as Security Markers Applied on the Surface of the Security Paper Intended for Printing Passports This example uses a round paper machine and an aqueous dispersion of cellulose fibers suitably bleached and refined in previous production processes along with different chemical products such as anti-foaming agents, charge retention agents, color fixing agents, mineral fillers such as titanium dioxide or alumina silicate, pigment dyes, ion and pH regulators and dry resistance resins such as carboxymethyl cellulose (all of them being added in specific amounts depending on the characteristics of the paper to be manufactured which amounts are not mentioned as they are not relevant to the properties to be achieved with the security markers), form the base pulp for manufacturing paper with a consistency or concentration around 3% by weight with respect to the amount of water used with pH between 7 and 8.

Wet resistance resin based on polyamide-epichlorohydrin which is also strongly cationic and has the possibility of forming covalent bonds similar to that indicated is subsequently added to the paper pulp, and such bonds are formed with as many cellulose fibers are left with this option and it also forms such bonds with itself to form the polymer lattice necessary to render the paper with the specified wet resistance level.

This entire mass of cellulose fibers and chemical additives subsequently arrive from the machine head ink to the round shape where the layer of paper is formed after the pressing and drying processes.

After drying, the paper will move to the gluing area where it will be immersed in a tray that will contain a dilution of gluing agents based on polyvinyl alcohol (reference Airvol 103 manufactured by Air Products & Chemical) where 100 ml of aqueous solution of $Au_{3-5}$—$Au_{15}$ charge-transfer complexes obtained in Example 1 suitably functionalized to have the capacity to form covalent bonds with the oxygen atoms of the hydroxyl groups of the gluing agent will have been added for every 100 liters of gluing agent.

The paper is subsequently dried and calendered until obtaining absolute moisture of the paper of 5%. The paper manufactured by these means is subsequently used for printing passports.

Example 6

Use of Nanosystems of $Au_{3-5}$—$Au_{15}$ Charge-Transfer Complexes as Security Markers Applied in the Coated Layer of Paper Intended for Printing Self Adhesive Security Labels This example uses a knife coating machine which is supplied with a coating slip previously prepared according to the following specially indicated formula for the use of the coated paper in offset printing techniques for self-adhesive security labels.

Mineral fillers: 80% calcium carbonate (Ref Albacar HO Slurry manufactured by Specialty Minerals) and 20% kaolin (reference Supragloss 95 manufactured by Imerys) to obtain 50 parts of the slip.

Synthetic binder: 10 parts butadiene styrene latex (reference Styronal D-517 manufactured by BASF).

Synthetic co-binder: 2 parts (reference Acronal 700 L manufactured by BASF).

Thickener: 1 part carboxymethyl cellulose.

Insolubilizing agent: 1 part (reference Basocoll OV manufactured by BASF).

Additives: 1 part sodium hydroxide.

Aqueous solution of $Au_{3-5}$—$Au_{15}$ charge-transfer complexes obtained in Example 1: 1 part.

Water: The rest up to 100 parts.

The Self-Adhesive Paper to be Coated has the Following Characteristics:

Total grammage: 200 g/m$^2$

Grammage of siliconized support: 82 g/m$^2$

Grammage of adhesive: 20 g/m$^2$

Fibrous composition of the front side: 100% cellulose from mechanical pulp

Conditions of the Coating Machine:

Drying tunnel temperature: 145° C.

Machine speed: 150 m/min

Residual moisture of the paper after drying: 6.5%

Characteristics of the Coated Paper:

Total grammage: 220 g/m$^2$

Grammage of coated layer: 20 g/m$^2$

Bekk smoothness on the coated side: 200 sec

Ash: 20%

Opacity: 84%

Implementation Method:

Once the coating machine is started up to reach the established machine conditions, the reel of paper is placed on the unwinding screw and the web of paper is distributed in the machine circuit, the coating slip is metered into the tray of the knife coater and the coating process begins according to the established machine conditions until finishing the reel.

After the coating process, the reel of paper is calendered until reaching the smoothness established and is cut to the format necessary for the subsequent process of sheet or reel printing of the security labels.

Example 7

Use of $Au_{3-5}$—$Au_{15}$ Charge-Transfer Complexes as Security Markers Applied in the Security Fiber Mass Intended for Inclusion in Security Paper Mass This example uses a plastic material extrusion machine made up of a metering hopper with circular section where the chips of polymer material will be metered, a piston meter where the $Au_{3-5}$—$Au_{15}$ charge-transfer complexes obtained in Example 1 will be metered, a single screw extruder with Maddock type mixer and spinning head, an air cooling system, a fiber tempering or tensing system and a cutter. The main process parameters in use and the configuration parameters of this machine are indicated below.

Configuration of the Screw of the Extruder:

Screw diameter: 5 cm

Screw length in the feeding area: 50 cm

Screw length in the compression area: 30 cm

Screw length in the metering area: 20 cm

Angle of the blades: 17.65°

Thread pitch: 5 cm

Gap between cylinder and screw: 0.5 cm

Depth of the metering channel; 0.25 cm

Depth of feeding channel 0.75 cm

Outer diameter of the cylinder: 7.01 cm

Inner diameter of the cylinder: 5.01 cm

Length of the mixer: 10 cm
Number of holes of the spinning head: 50
Diameter of the holes: 0.15 mm
Process Parameters of the Extruder:
Range of temperatures along the cylinder: 120-185°
Fiber flow rate at the outlet of the spinning head: 10 l/h
Output speed: 3.14 m/s (7.5 kg of fiber/hour)
Characteristics of the Polymer Material:
Composition: polypropylene manufactured by LyonDell-Basell (ref.: HM560R)
Chip density: 0.91 g/cm$^3$
Melting temperature: 145° C.
Fluidity Index: 25 g/10 min (230° C./2.16 kg)
Characteristics of the Security Fibers:
Thickness: 0.02 mm
Length 3 mm
Implementation Method:

Once the extrusion machine is started up in the indicated configuration and process parameters, coat to reach the established machine conditions, the heated hopper is fed with the polypropylene chips. The markers with $Au_{3-5}$—$Au_{15}$ charge-transfer complexes obtained in Example 1 will be introduced by using a vertical piston meter located between the feeding area and the compression area of the extruder. The material is gradually mixed and pressed as it moves along the screw starting with an atmospheric pressure in the hopper and increasing until the outlet through the nozzle. Before reaching the mixer, the components pass through a mesh or filter. After going through the mixer the material is subjected to maximum pressure and passes through a spinning head provided with small holes where the fibers will be produced.

Once the fibers are obtained, they must be cooled by means of an air current and are subsequently collected by a drive roller feeding the tensing unit. In this unit the fibers align their crystalline structure in the direction of the axis of the filament enabling their lengthening which will be produced through the action of a roller which is at the end of the drying chamber and which rotates at a speed 4 times faster than that of the outlet of the spinning head.

Then another roller will drive the fibers to the cutting machine where a set of stationary blades will cut the fibers into the specific length.

Example 8

Use of Nanosystems of $Au_{3-5}$—$Au_{15}$ Charge-Transfer Complexes as Security Markers Applied in Silk-Screen Printing Ink of Polymeric Substrates for Identification Cards This example use a silk-screen printing machine jointly manufactured by Stork and Thieme with ultraviolet drying, a Rotaplate silk screen manufactured by Stork, polyester-based polymeric substrate, silk-screen printing ink manufactured by Sicpa and a aqueous solution of $Au_{3-5}$—$Au_{15}$ charge-transfer complexes obtained in Example 1.

The main characteristics of the installations and materials indicated are described below:
Conditions of the Printing Machine on Each Side of the Paper:
Machine speed: 4000 sheets/hour
Conditions of drying: 60%
Conditions of the Silk Screen Rotaplate 125 W
Mesh: 125 hpi
Thickness: 120 microns
Open area: 43%
Diameter: 140 microns
Conditions of the Iridescent Ink and Additives:
Commercial name of the ink: Silk-screen printing ink 3Z1Q09
Viscosity of the printing ink: 120 s CP4
Main Conditions of the Polymeric Substrate:
Composition: polyester manufactured by PPG Industries (Ref.: Teslin SP 1000)
Thickness: 200 microns
Implementation Method:

Once the printing machine is started up to reach the established machine conditions, the silk screen is placed and those of polyester are positioned, a mixture of silk-screen printing ink to which 100 ml of the aqueous solution of $Au_{3-5}$—$Au_{15}$ charge-transfer complexes obtained in Example 1 will have been previously added will be pumped to the inkwell. The printing of the ink through the holes of the screen according to the graphic design established therein on one of the sides, controlling the viscosity of the ink and the machine conditions throughout the entire printing process is subsequently started.

Example 9

Use of Nanosystems of $Au_{3-5}$—$Au_{15}$ Charge-Transfer Complexes as Security Markers Applied in the Coated Layer of Paper Intended for Printing Postal Mail Stamps This example uses a filmpress coating machine which is supplied with a coating slip previously prepared according to the following formula such that the type and characteristics of the coating obtained is specially indicated for a use of the coated paper in gravure printing techniques for postal mail stamps Mineral fillers: 50 parts kaolin (reference Supragloss 95 manufactured by Imerys).
Synthetic binder: 12 parts butadiene styrene latex (reference L-8000 manufactured by EOC Polymers).
Synthetic co-binder: 2 parts (reference Acronal 700 L manufactured by BASF).
Thickener: 1 part of carboxymethyl cellulose.
Insolubilizing agent: 1 part (reference Basocoll OV manufactured by BASF).
Additives: 1 part sodium hydroxide.
Aqueous solution of $Au_{3-5}$—$Au_{15}$ charge-transfer complexes obtained in Example 1: 1 part.
Water: The rest up to 100 parts.
The Support Paper to be Coated has the Following Characteristics:
Total grammage: 90 g/m$^2$
Thickness: 120 microns
Fibrous composition: 100% cellulose from mechanical pulp
Conditions of the Coating Machine:
Drying tunnel temperature: 150° C.
Machine speed: 170 m/min
Residual moisture of the paper after drying: 5.5%
Characteristics of the Coated Paper:
Total grammage: 110 g/m$^2$
Grammage of coated layer: 20 g/m$^2$
Bekk smoothness on the coated side: 1800 sec
Ash: 15%
Opacity: 80%
Implementation Method:

Once the coating machine is started up to reach the established machine conditions, the reel of paper is placed on the unwinding screw and the web of paper is distributed in the machine circuit, the coating slip is metered into the tray for supplying the cylinders in contact with the paper and the coating process begins according to the established machine conditions until finishing the reel.

After the coating process, the reel of paper is calendered until reaching the established smoothness and is cut to the format necessary for the subsequent process for sheet or reel printing of postal mail stamps.

Example 10

Use of Nanosystems of $Au_{3-5}$—$Au_{15}$ Charge-Transfer Complexes as Security Markers Applied in the Gummed Layer of Paper Intended for Printing Gummed Tax Stamps or Security Labels This example uses a filmpress coating machine which is supplied with a slip of previously conditioned re-wettable gum which is specially indicated for the use of gummed paper for offset printing techniques for gummed tax stamps or security labels.

The slip of re-wettable gum used is based on polyvinyl acetate, reference A-4524 manufactured by Henkel Adhesives & Technologies. 1 liter of aqueous dispersion of $Au_{3-5}$—$Au_{15}$ charge-transfer complexes obtained in Example 1 and 1400 grams of green food dye with reference Verde Carta DAM Líquido manufactured by Clariant previously prepared by mixing 1 part of the dye indicated with 3 parts water are added for every 1000 kg tank of gum slip The Support Paper to be Gummed has the Following Characteristics:
 Total grammage: 95 g/m²
 Thickness: 98 microns
 Fibrous composition: 100% cellulose from mechanical pulp
Conditions of the Coating Machine:
 Drying tunnel temperature: 130° C.
 Machine speed: 140 m/min
 Residual moisture of the paper after drying: 5.5%
Characteristics of the Gummed Paper:
 Total grammage: 105 g/m²
 Grammage of coated layer: 10 g/m²
 Re-wettable gum adhesion: 25 gF/mm
 Ash: 10%
 Opacity: 80%
Implementation Method:

Once the coating machine used to apply the re-wettable gum is started up to reach the established machine conditions, the reel of paper is placed on the unwinding screw and the web of paper is distributed in the machine circuit, the gum slip is metered into the tray for feeding the cylinders in contact with the paper and the gumming process begins according to the established machine conditions until finishing the reel.

After the gumming process, the reel of paper is cut to the format necessary for the subsequent process for sheet or reel printing of the gummed tax stamps or security labels.

Example 11

Use of $Au_{3-5}$—$Au_{15}$ Charge-Transfer Complexes as Security Markers Applied on the Surface in Cellulose Tapes for Insertion into the Security Paper Mass Intended for Printing Legal Tender Notes This example uses a gravure printing machine manufactured by Giave, a gravure cylinder manufactured by Artcyl and etched by Ziraba, natural cellular-based fibrous paper manufactured by Miguel and Costas, gravure ink manufactured by Sicpa and a aqueous solution of $Au_{3-5}$—$Au_{15}$ charge-transfer complexes obtained in Example 1.

The main characteristics of the installations and materials indicated are described below:
Conditions of the Printing Machine on Each Side of the Paper:
 Drying tunnel temperature: 45° C.
 Machine speed: 80 m/min
 Reel tension: 150 N
 Heliofun (antistatic system): 60%
Conditions of the Gravure Cylinder
 Type of etching: chemical
 Lineature: 90 line/cm
 Cell depth: 34 microns
 Table: 510 mm
 Diameter: 24"=194.02 mm
Conditions of the Ink:
 Commercial name of the ink: 67E9011
 Viscosity of the ink: 32 s CP4
 Viscosity of the varnish for application: 32 s CP4
Main Conditions of the Paper:
 Fibrous composition: 100% cellulose
 Grammage: 18 g/m²
 Thickness: 30 microns
 Bendtsen porosity: 144 ml/min
 Opacity: 25%
Implementation Method:

Once the printing machine is started up to reach the machine conditions, the gravure cylinder is placed on the unwinding screw and the web of paper is distributed in the machine circuit the ink is mixed with 100 ml of the aqueous solution of $Au_{3-5}$—$Au_{15}$ charge-transfer complexes obtained in Example 1. Once the perfect dispersion of the components is assured, the content of the drum is pumped to the inkwell of the printing machine. The paper is positioned on the printing cylinder starting the printing of the ink on the paper on one of the sides, controlling the final moisture of the paper, viscosity of the ink and the machine conditions throughout the entire printing process. After the process ends the reel is left at rest for a minimum development time of 24 hours at room temperature (23° C. and 50% RH).

The invention claimed is:

1. A method of marking a document, article, or element for security enhancement thereof, said method comprising incorporating in said document, article, or element, a charge-transfer complex of at least two different size metal atomic quantum clusters (AQCs), $M_n$ and $M'_{n'}$, of general formula (I):

$$M_n^+ M'_{n'}{}^- \qquad (I),$$

wherein
 the metals, M and M', of the metal AQCs are the same or different metals,
 $M_n$, is the smaller AQC which is present in its oxidized form, $M_n^+$,
 $M'_{n'}$, is the larger AQC which is present in its reduced form, $M'_{n'}{}^-$,
 $M_n^+$ and $M'_{n'}{}^-$ are bound by electrostatic interactions,
 n and n' are respectively the number of metal atoms of M and M', and
 n is smaller than n'
 as a marker for said document, article or element.

2. The method according to claim 1, wherein the same or different metals, M and M', of the metal atomic quantum clusters are selected from transition metals or combinations thereof.

3. The method according to claim 2, wherein the same or different metals, M and M', of the metal atomic quantum clusters are selected from the transition metals Au, Ag, Cu and combinations thereof.

4. The method according to claim 2, wherein the same or different metals, M and M', of the metal atomic quantum clusters are selected from the transition metals Au, Ag and combinations thereof.

5. The method according to claim 1, wherein the number of metal atoms, n and n', of the at least two different size metal atomic quantum clusters are in a range selected from the group of ranges consisting of: (i) between 2 and 309 metal atoms ($M_n$, $2 \leq n \leq 309$), (ii) between 2 and 102 metal atoms ($M_n$, $2 \leq n \leq 102$), (iii) between 2 and 55 metal atoms ($M_n$, $2 \leq n \leq 55$) and (iv) between 2 and 25 metal atoms ($M_n$, $2 \leq n \leq 25$).

6. The method according to claim 1, wherein the difference between n and n' is between 5 and 50 atoms.

7. The method according to claim 1, wherein the charge-transfer complex additionally comprises ω-hydroxyacids and ω-mercaptoacids ligands attached to the atomic quantum clusters, $M_n$ and $M'_{n'}$.

8. The method according to claim 1, wherein after exciting the charge-transfer complex by an external excitation source luminescence, is produced in the charge-transfer complex.

9. The method according to claim 8, wherein the Stokes shift of the charge-transfer complex produced after exciting the charge-transfer complex by an external excitation source, is greater than approximately 150 nm.

10. The method according to claim 9, wherein the Stokes shift is greater than approximately 300 nm.

11. The method according to claim 8, wherein the external excitation source luminescence comprises fluorescence.

12. The method according to claim 1, wherein the fluorescent charge-transfer complex has a decaying time greater than 0.1 microsecond.

13. The method according to claim 12, wherein the fluorescent nanosystem has a decaying time greater than one microsecond.

14. A security element, article or document which comprises a charge-transfer complex of at least two different size metal atomic quantum clusters (AQCs), $M_n$ and $M'_{n'}$, of general formula (I):

$$M_n^+ M'^-_{n'} \qquad (I),$$

wherein
the metals, M and M', of the metal AQCs are the same or different metals,
$M_n$, is the smaller AQC which is present in its oxidized form, $M_n^+$,
$M'_{n'}$, is the larger AQC which is present in its reduced form, $M'^-_{n'}$,
$M_n^+$ and $M'^-_{n'}$ are bound by electrostatic interactions,
n and n' are respectively the number of metal atoms of M and M', and
n is smaller than n'.

15. The security element according to claim 14 selected from substrate body, security threads, security fibers, watermarks, tactile effects, security cellulose strips, layers of glues, lacquers, plasters, planchettes, holograms, security inks and plastic sheets.

16. The security document or article according to claim 14 selected from security paper, envelopes, cheques, bank notes, identity documents, tickets, stamps, admission passes, impressed and certified papers.

17. A method of manufacturing an element, document or article as defined in claim 14, comprising incorporating therein a charge-transfer complex of at least two different size metal atomic quantum clusters (AQCs), $M_n$ and $M'_{n'}$, of general formula (I):

$$M_n^+ M'^-_{n'} \qquad (I),$$

wherein
the metals, M and M', of the metal AQCs are the same or different metals,
$M_n$, is the smaller AQC which is present in its oxidized form $M_n^+$,
$M'_{n'}$, is the larger AQC which is present in its reduced form, $M'^-_{n'}$,
$M_n^+$ and $M'^-_{n'}$ are bound by electrostatic interactions,
n and n' are respectively the number of metal atoms of M and M', and
n is smaller than n'
  i) during the manufacturing of the material used to manufacture the document or article,
  ii) as part of an additive which is added to the element, document or article,
  iii) on the surface of said article or document, or
  iv) as part of one or more of dyes or inks used in manufacturing of the document or article.

18. A method for determining the authenticity of a document, article or element as defined in claim 14, comprising:
(a) irradiating the document, article or element with an external excitation source at a pre-determined excitation wavelength, $\lambda_{exc.}$ to excite the charge-transfer complex, and
(b) detecting one or more of the following parameters:
emission wavelength ($\lambda_{em.}$),
intensity,
mean lifetime,
anisotropy,
of said charge-transfer complex.

* * * * *